(12) United States Patent
Chen

(10) Patent No.: US 8,080,012 B2
(45) Date of Patent: Dec. 20, 2011

(54) ULTRASONIC SINUS MEMBRANE/PERIOSTEUM SEPARATION TOOL SET

(76) Inventor: Chun-Leon Chen, Changhua (TW)

(*) Notice: Subject to any disclaimer, the term of this patent is extended or adjusted under 35 U.S.C. 154(b) by 147 days.

(21) Appl. No.: 12/725,921

(22) Filed: Mar. 17, 2010

(65) Prior Publication Data

US 2011/0229846 A1    Sep. 22, 2011

(51) Int. Cl.
*A61F 2/46* (2006.01)
(52) U.S. Cl. ....................................... 606/86 R
(58) Field of Classification Search ............. 606/86 R; 604/22; 433/144
See application file for complete search history.

(56) References Cited

U.S. PATENT DOCUMENTS

2009/0004624 A1    1/2009    Lee

*Primary Examiner* — Thomas C. Barrett
*Assistant Examiner* — Sameh Boles
(74) *Attorney, Agent, or Firm* — Guice Patents PLLC

(57) ABSTRACT

An ultrasonic sinus membrane/periosteum separation tool set consisting of a cutting tool and a spray nozzle for use with a hand piece of an ultrasonic machine is disclosed. The cutting tool has a connection base, a pole and a cutter tip. The spray nozzle has a connection base, a pole and an operating tip. The pole extends from the connection base, having a longitudinal fluid passage for the passing of a fluid and a fluid injection hole for injecting a fluid into a hole made on the alveolar ridge of the gingiva of the patient to be treated. The cutter tip and the operating tip each have jet holes for ejecting a fluid radial in jets, facilitating sinus augmentation (sinus lift or sinus graft). The ultrasonic sinus membrane/periosteum separation tool set can also be used in an upper/lower jaw deformity implant surgery.

4 Claims, 15 Drawing Sheets

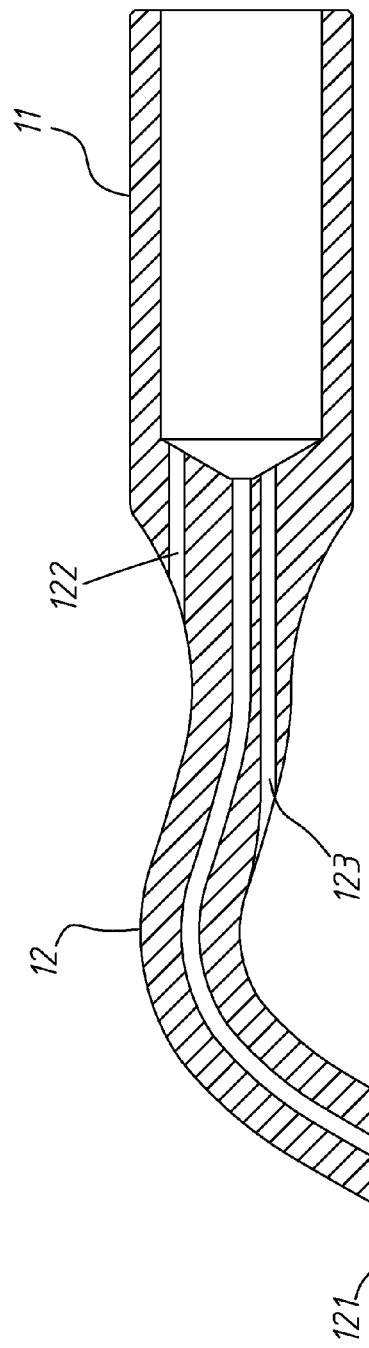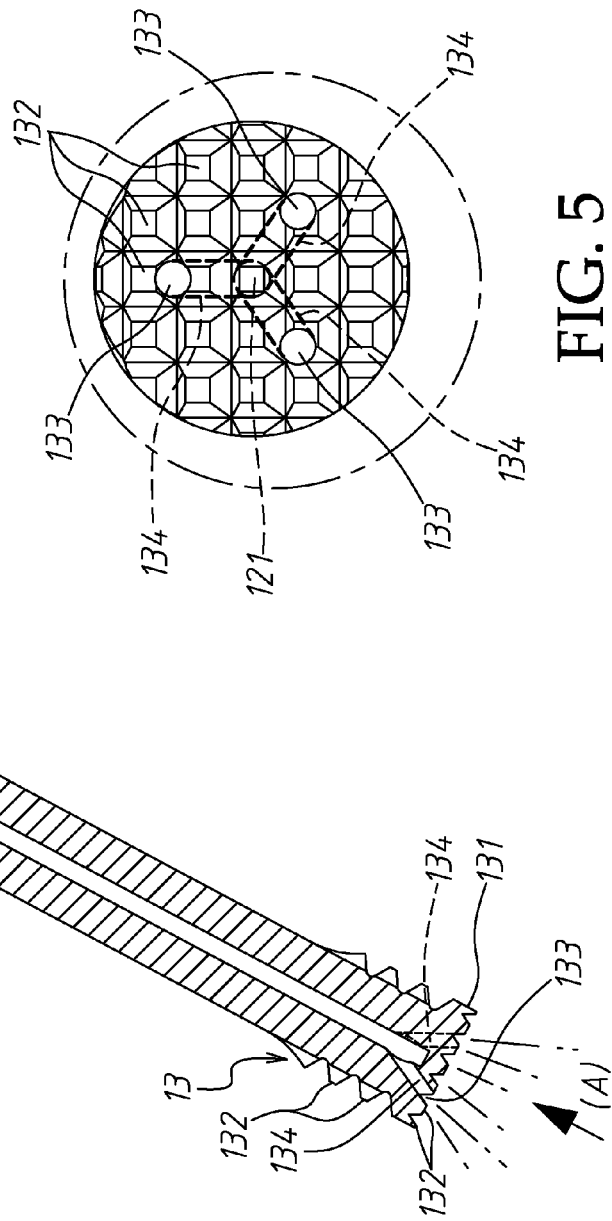

ULTRASONIC SINUS MEMBRANE/PERIOSTEUM SEPARATION TOOL SET

BACKGROUND OF THE INVENTION

1. Field of the Invention

The present invention relates to medical instruments and more particularly, to an ultrasonic sinus membrane/periosteum separation tool set, which facilitates sinus augmentation on a steeply inclined sinus membrane in a dental implant surgery, and is practical for use in an upper/lower jaw deformity implant surgery, raising the success rate of dental implants.

2. Description of the Related Art

During a dental implant surgery, an implant is implanted in the gingiva, and then a crown is affixed to the implant. If the elevation of the patient's gingival is insufficient, the implant surgery could not be performed.

The inventor disclosed the use of certain tools for sinus augmentation, such as piezo insert and piezo packer. The piezo insert is inserted into a hole on the alveolar ridge to separate the sinus membrane by means of a water pressure, and then the piezo packer is used to fill a bone powder into the hole to increase the elevation for the implantation of an implant.

US Patent Application Publication No. 2009/0004624 A1, entitled "Piezo Insert and Piezo Packer for Operating an Implant Surgical Operation Using Piezoelectric Device", teaches the use of a piezoelectric device. As shown in FIG. 1, the piezoelectric device comprises a piezoelectric main device 10, a hand piece 20, a piezo insert 30 and a piezo packer 40. The piezo insert 30 has a body, which is connectable with its one end to the hand piece of the piezoelectric main device, a pole extended from the other end of the body, and an insert tip located on the distal end of the pole. The insert tip has a plurality of holes that are located on the end face of the insert tip to enhance vertical cutting force. The piezo packer 40 has a body, which is connectable with its one end to the hand piece of the piezoelectric main device, a pole extended from the other end of the body, and a tip located on the distal end of the pole. The tip of the piezo packer has a plurality of cutting protrusions that are arranged on the end face of the tip to enhance bone cutting force and to transfer vibrations to an implant material.

According to the aforesaid prior art design, the piezo packer simply has the cutting protrusions arranged on the end face for cutting and a jet hole located at the center of the end face for the ejection of a fluid. This tool is not practical for a sinus augmentation surgery on a deeply inclined sinus membrane. As shown in FIG. 1, when the tip 93 of the prior art piezo packer is inserted into a hole 92 on the alveolar ridge 91, the vertical fluid jets from the tip 93 cannot effectively separate the steeply inclined sinus membrane 94. Further, because the tip has all its cutting protrusions arranged on the end face, the tip may be unable to cut off the residual bone at the bottom side of the sinus membrane 94 (see the location indicated by reference sign 95). Carelessness may cause the tip to punch through the sinus membrane 94 at the location indicated by reference sign 96. Therefore, an improvement is necessary.

SUMMARY OF THE INVENTION

The present invention has been accomplished under the circumstances in view. It is therefore the main object of the present invention to provide an ultrasonic sinus membrane/periosteum separation tool set, which facilitates sinus augmentation on a steeply inclined sinus membrane in a dental implant surgery. It is another object of the present invention to provide an ultrasonic sinus membrane/periosteum separation tool set, which is practical for use in an upper/lower jaw deformity implant surgery, raising the success rate of dental implants.

To achieve these and other objects of the present invention, an ultrasonic sinus membrane/periosteum separation tool set is adapted for connection to a hand piece of an ultrasonic machine for use in a dental implant surgery, comprising a cutting tool and a spray nozzle. The cutting tool comprises a connection base connectable to the hand piece of the ultrasonic machine, a pole that extends from the connection base, having a longitudinal fluid passage extending through the two distal ends thereof for the passing of a fluid provided by the ultrasonic machine and a fluid injection hole for ejecting a fluid into a hole made on the alveolar ridge of the gingiva of the patient to be treated, and a cutter tip located on one end of the pole remote from the connection base. The cutter tip has an end face, a plurality of protruding cutting edges raised from the end face and the periphery thereof, three jet holes located on the end face and a plurality of oblique manifolds respectively connected between the jet holes and the longitudinal fluid passage of the pole. The spray nozzle comprises a connection base, a pole that extends from the connection base and has a longitudinal fluid passage extending through the two distal ends thereof for the passing of a fluid provided by the ultrasonic machine and a fluid injection hole for ejecting a fluid into a hole made on the alveolar ridge of the gingiva of the patient to be treated, and an operation tip located on one end of the pole remote from the connection base for transferring ultrasonic waves from the ultrasonic machine to the fluid filled in a hole made on the alveolar ridge of the gingiva of the patient to be treated. The operation tip has a plurality of jet holes located on an end face and the periphery thereof and respectively connected to the longitudinal fluid passage of the pole.

The ultrasonic sinus membrane/periosteum separation tool set facilitates sinus augmentation on a steeply inclined sinus membrane in a dental implant surgery.

Further, a cooling fluid passage may be made on the junction between the connection base and pole for the passing of a cooling fluid to cool down the temperature of the junction.

BRIEF DESCRIPTION OF THE DRAWINGS

FIG. 4 is a sectional view of the cutting tool according to the present invention.

FIG. 5 is a plain view in an enlarged scale in direction A of FIG. 4.

DETAILED DESCRIPTION OF THE PREFERRED EMBODIMENT

Figure 2:
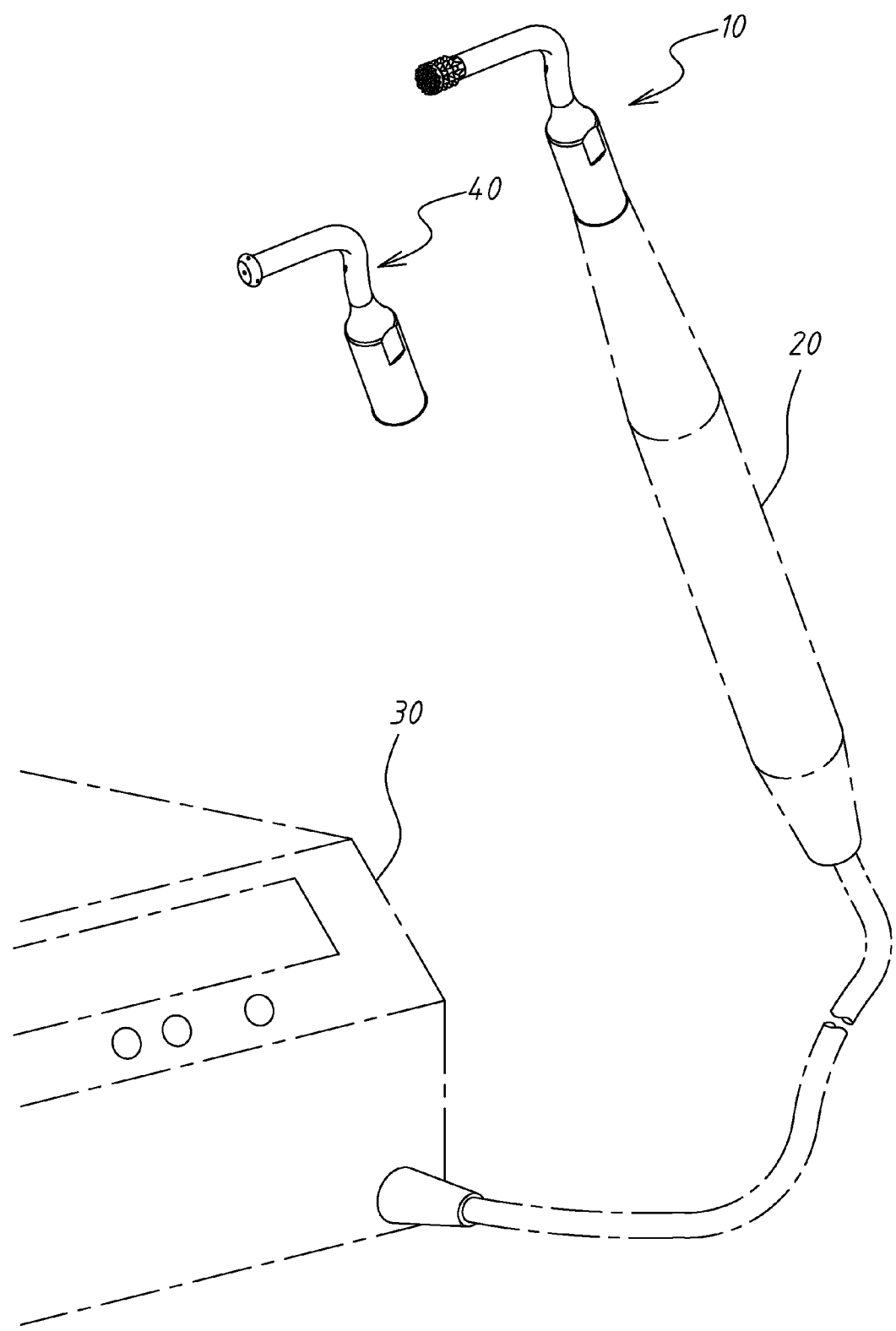
FIG. 2 is a schematic drawing showing an ultrasonic sinus membrane/periosteum separation tool set used with the hand piece of an ultrasonic machine according to the present invention.

Referring to FIG. 2, an ultrasonic sinus membrane/periosteum separation tool set in accordance with the present invention is shown comprising a cutting tool 10 and a spray nozzle 40. The cutting tool 10 and the spray nozzle 40 are selectively attachable to a hand piece 20 of an ultrasonic machine 30 to provide vibrations or jets of a fluid.

Figure 1:
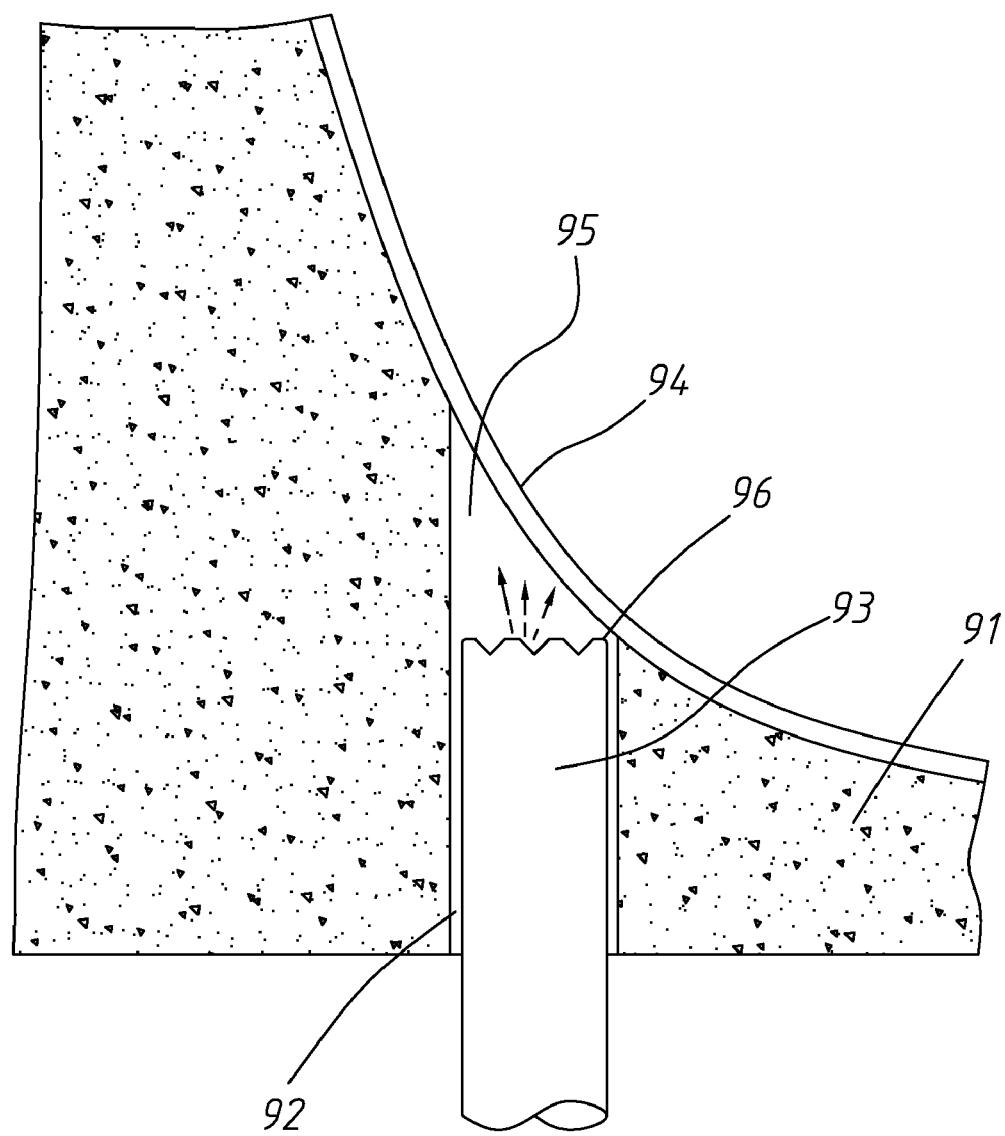
FIG. 1 is a schematic drawing showing a packer worked in a gingiva according to the prior art.
Figure 3:
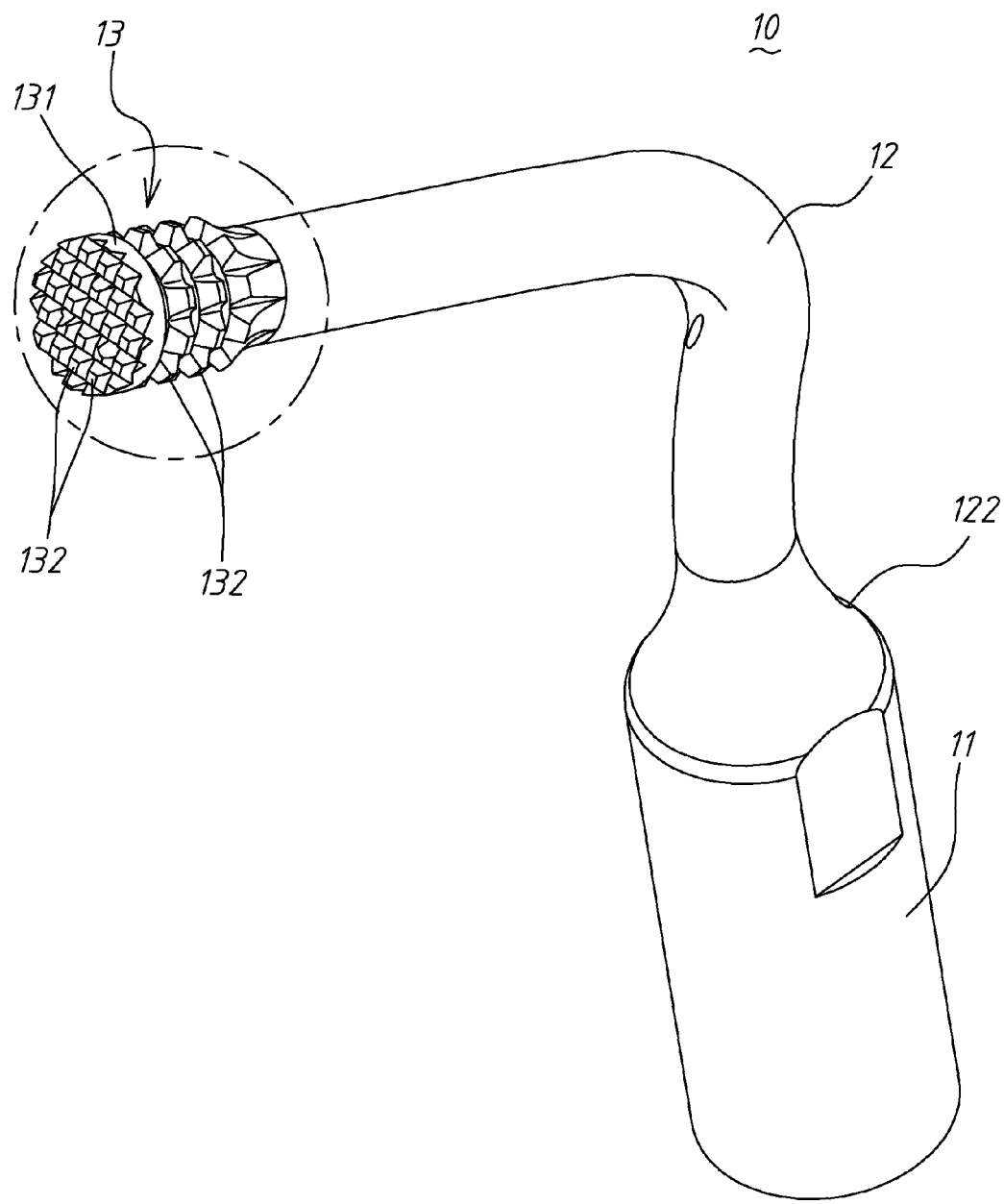
FIG. 3 is an elevational view of the cutting tool according to the present invention.

Referring to FIG. 3 and FIGS. 1 and 2 again, the cutting tool 10 has a connection base 11, a pole 12 and a cutter bit 13. The connection base 11 has its one end configured for connection to the hand piece 20 of the ultrasonic machine 30. The pole 12 extends from the other end of the connection base 11, having a longitudinal fluid passage 121 that extends through the two distal ends of the pole 12 (see FIG. 4), a fluid injection hole 123 for injecting a fluid into a hole 92 made on the alveolar ridge 91 of the patient to be treated. The pole 12 has a substantially L-shaped profile. The fluid injection hole 123 extends longitudinally through a part of the pole 12 adjacent to the turning angle of the L-shaped configuration. The cutter tip 13 is located on the distal end of the pole 12 remote from the connection base 11. Further, the cutter tip 13 is a cylindrical member having an end face 131 and a plurality of protruding cutting edges 132 raised from the end face 131 and the periphery thereof for transferring ultrasonic waves to the fluid in the hole 92 to produce vibrations for removing soft tissues. Further, as shown in FIG. 5, three jet holes 133 are located on the end face 131 and equiangularly spaced around the fluid passage 121. Further, these the jet holes 133 are respectively connected to the distal end of the longitudinal fluid passage 121 by a respective manifold 134 so that a fluid can be driven out of the end face 131 radially.

Referring to FIG. 4, the cutting tool 10 further has a cooling fluid passage 122 located on the junction between the connection base 11 and the pole 12 for the passing of a cooling fluid to cool down the temperature of this area.

Figure 6:
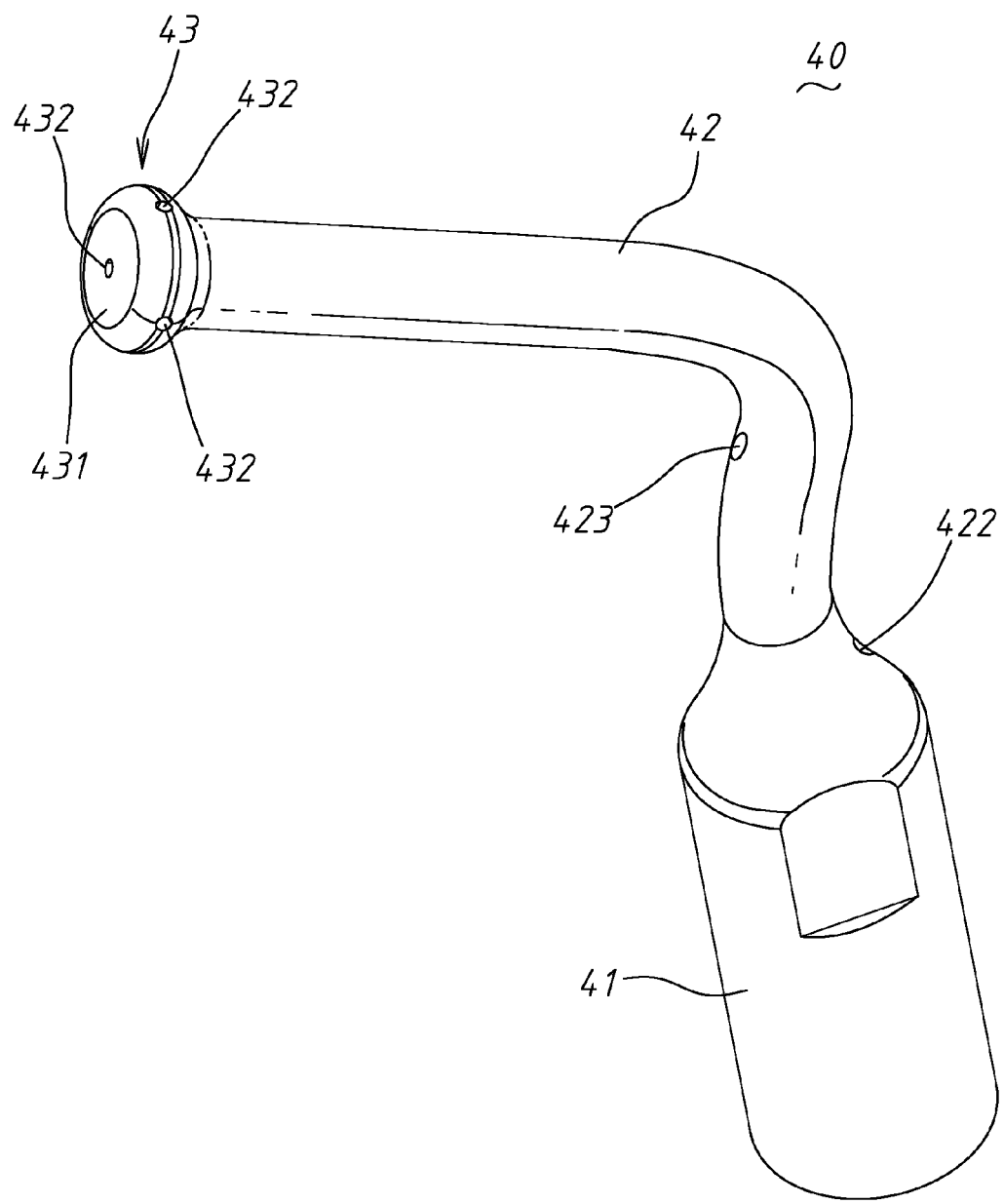
FIG. 6 is an elevational view of the spray nozzle according to the present invention.
Figure 7:
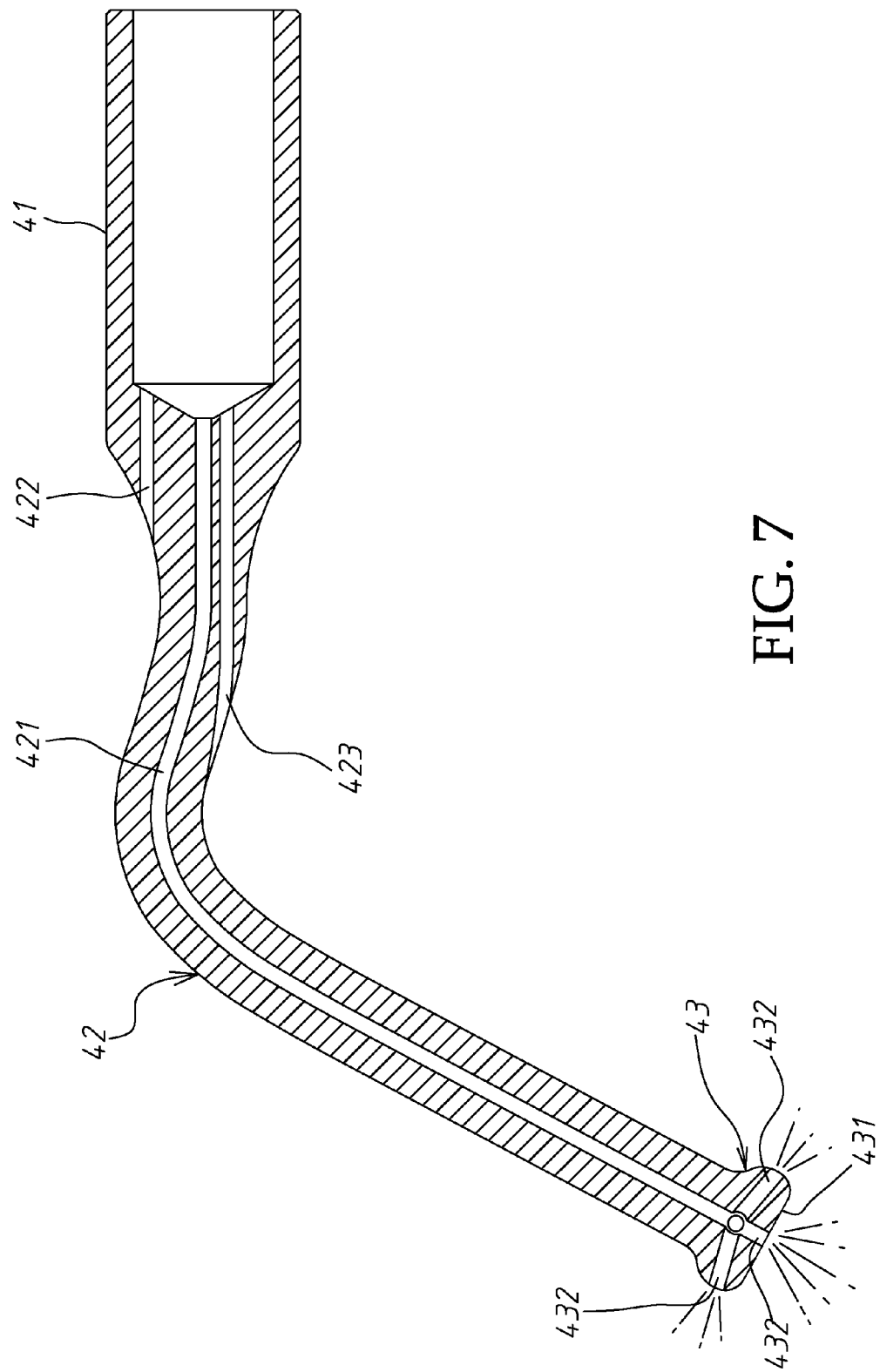
FIG. 7 is a sectional view of the spray nozzle according to the present invention.

Referring to FIGS. 6 and 7, the spray nozzle 40 has a connection base 41, a pole 42 and an operating tip 43.

The connection base 41 has its one end configured for connection to the hand piece 20 of the ultrasonic machine 30. The pole 42 extends from the other end of the connection base 41, having a longitudinal fluid passage 421 that extends through the two distal ends of the pole 42 (see FIG. 7) and a fluid injection hole 423 for injecting a fluid into a hole 92 made on the alveolar ridge 91 of the patient to be treated. The pole 42 has a substantially L-shaped profile. The fluid injection hole 423 extends longitudinally through a part of the pole 42 adjacent to the turning angle of the L-shaped configuration. The operating tip 43 is located on the distal end of the pole 42 remote from the connection base 41 for transferring ultrasonic waves to the fluid in the hole 92 to produce vibrations. Further, the operating tip 43 has an end face 131 and a plurality of jet holes 432 that are respectively located at the center of the end face 131 and equiangularly spaced around the periphery of the operating tip 43 and respectively connected to the distal end of the longitudinal fluid passage 421 for ejecting a fluid a fluid can be driven out of the end face 131 radially (see FIG. 7) to separate the sinus membrane or periosteum.

Referring to FIG. 7, the spray nozzle 40 further has a cooling fluid passage 422 located on the junction between the connection base 41 and the pole 42 for the passing of a cooling fluid to cool down the temperature of this area.

FIGS. 8~11 illustrate an application example of the present invention in a sinus augmentation (sinus lift or sinus graft).

Figure 8:
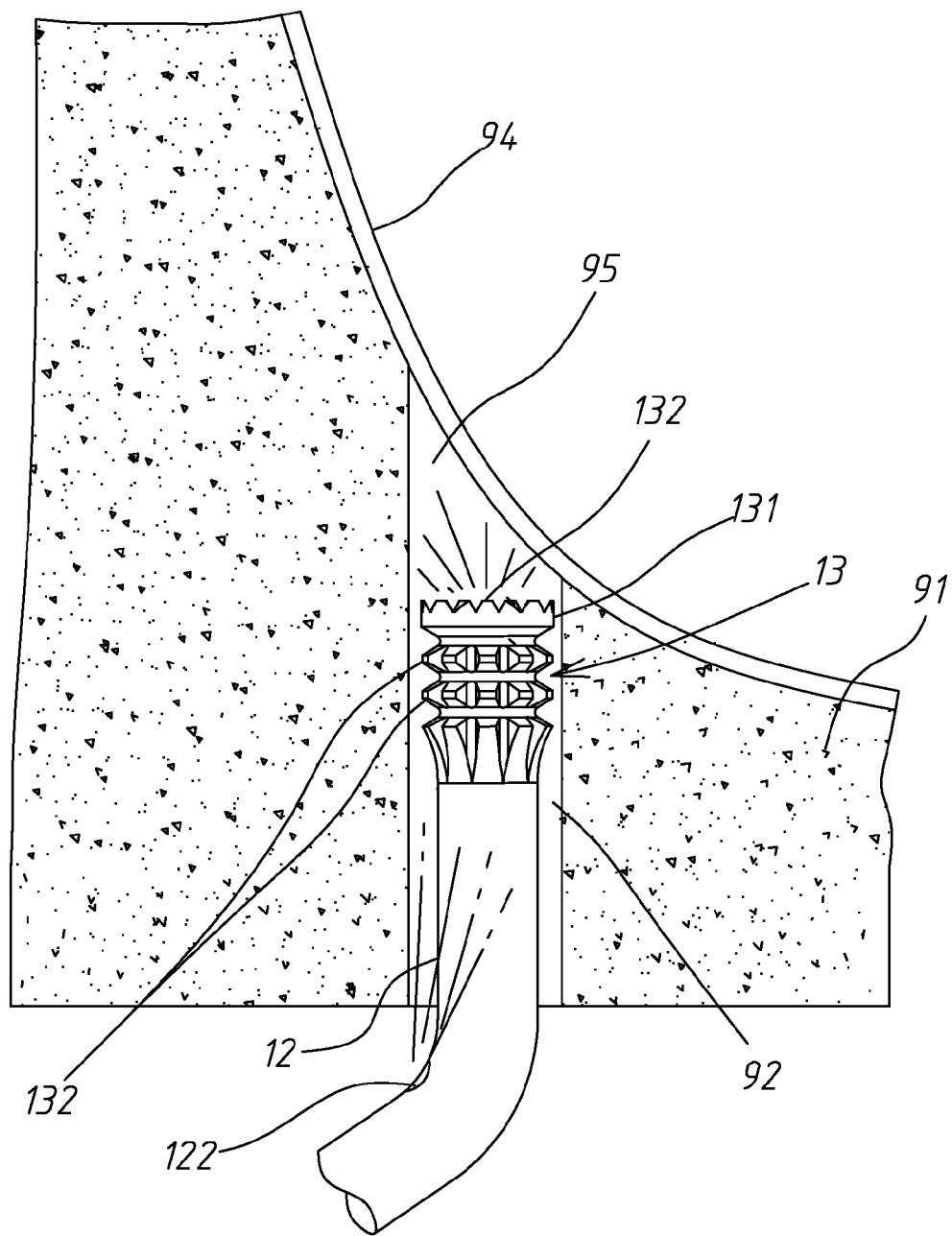
FIGS. 8~11 illustrate an application example of the ultrasonic sinus membrane/periosteum separation tool set in a sinus augmentation according to the present invention.

As shown in FIG. 8, the cutter tip 13 of the cutting tool 10 is inserted into the hole 92 on the alveolar ridge 91 and then biased to force the protruding cutting edges 132 against the residual bone and soft tissues (the location indicated by reference sign 95) under the sinus membrane 94, thereby removing the unnecessary residual bone and soft tissues. Thereafter, the ultrasonic machine 30 is controlled to drive a fluid out of the jet holes 133 at the end face 131 of the cutter tip 13 to lift the sinus membrane 94, and then the ultrasonic machine 30 is controlled to output ultrasonic waves, enabling ultrasonic waves to be transferred by the cutting tool 10 to the fluid in the hole 92 to produce vibrations and to further remove waste soft tissues out of the hole 92.

Figure 9:
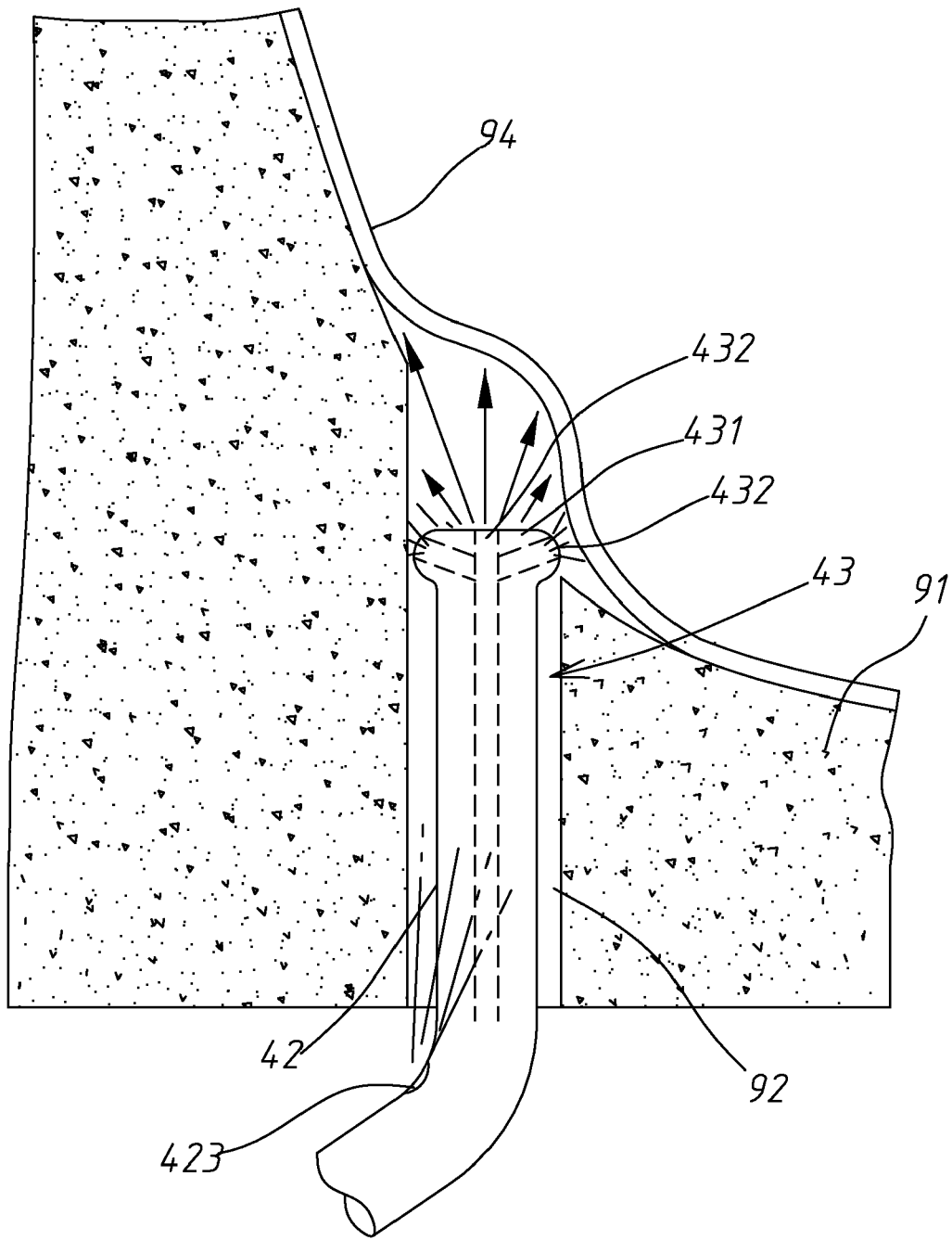

Thereafter, as shown in FIG. 9, the spray nozzle 40 is used to substitute for the cutting tool 10 and the operating tip 43 of the spray nozzle 40 is inserted into the hole 92 on the alveolar ridge 91 to eject a fluid out of the jet holes 432 and transfer ultrasonic waves, enhancing separation of the sinus membrane 94.

Figure 10:
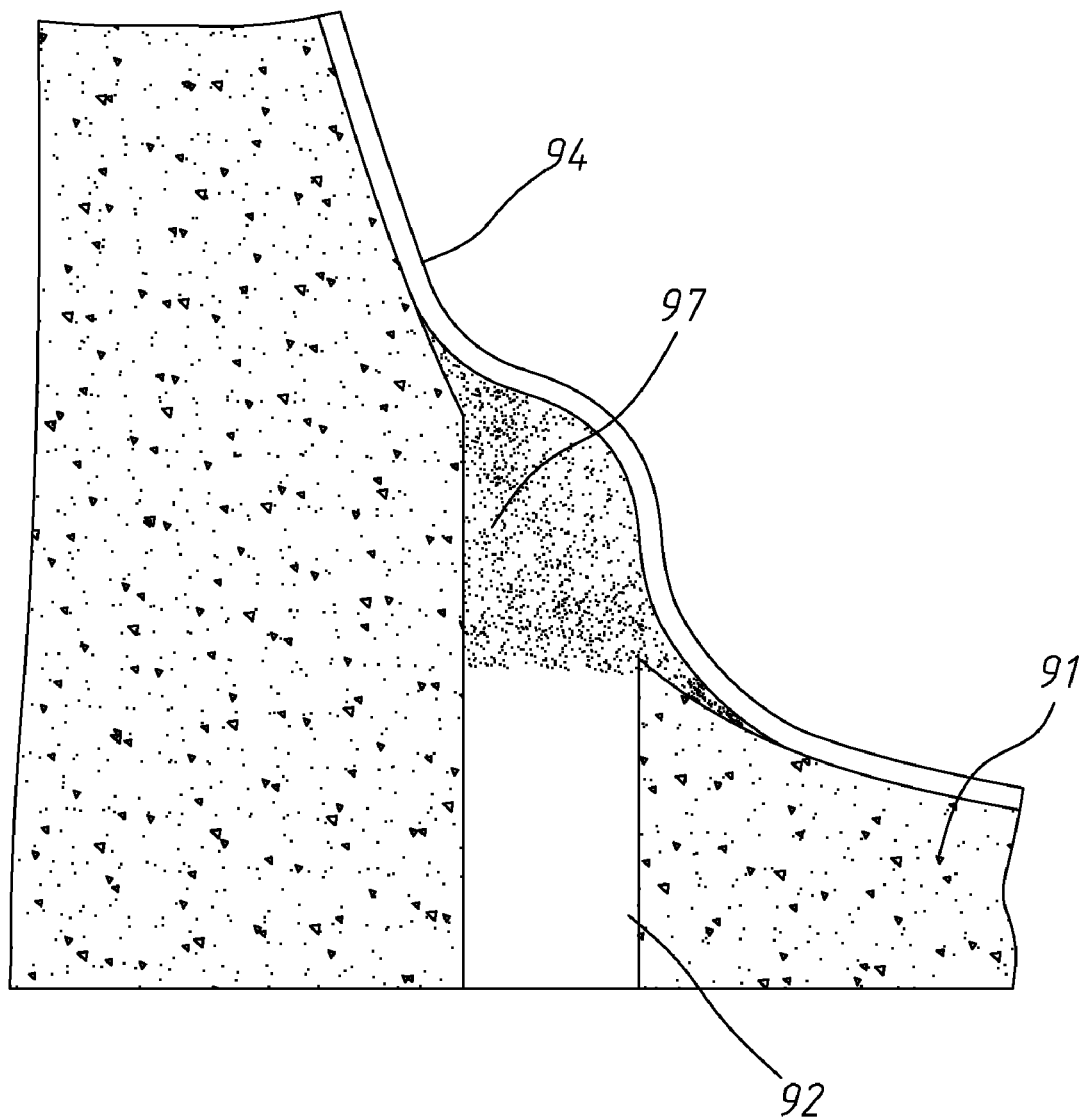
Figure 11:
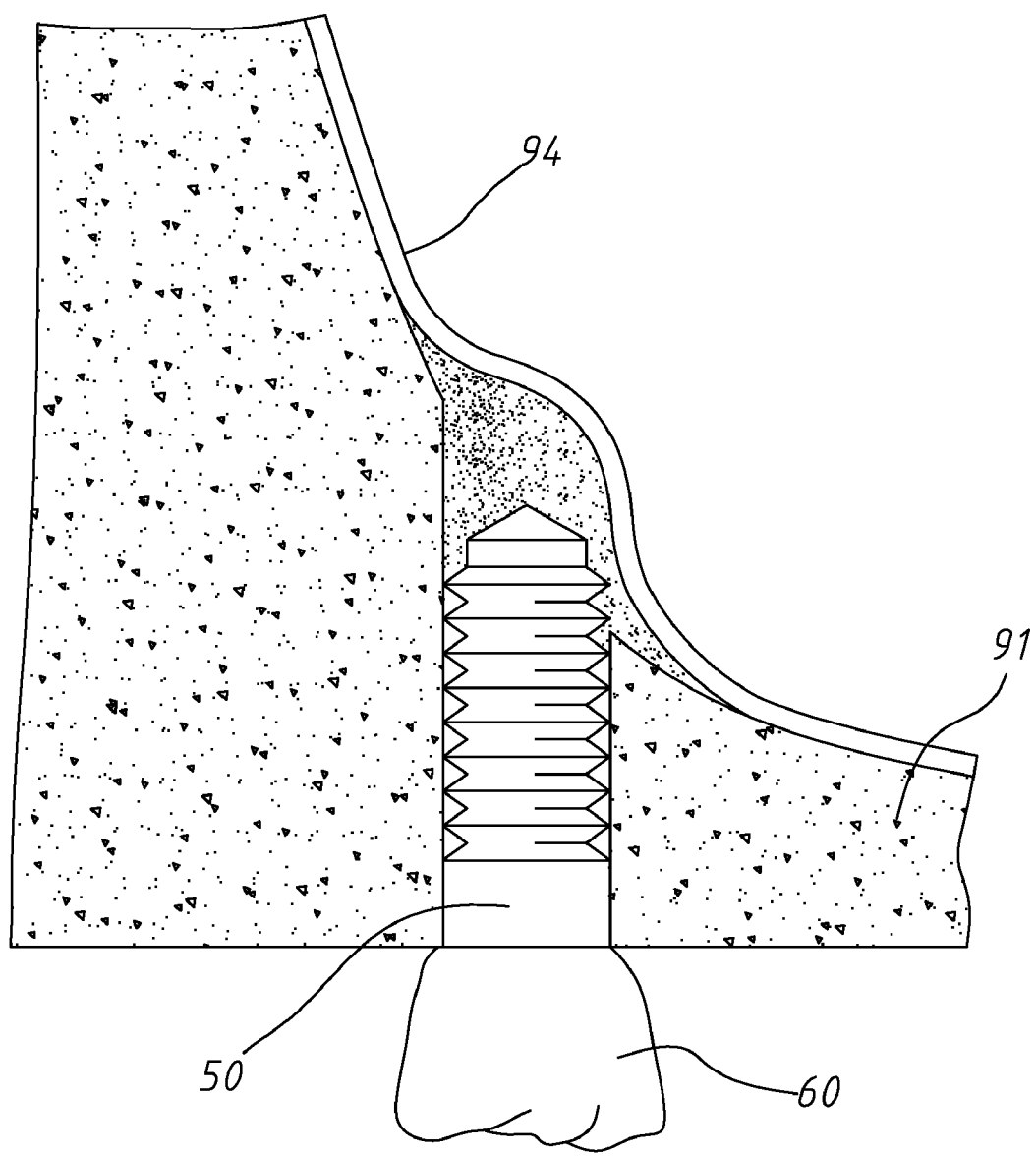

Thereafter, bone powder 97 is filled in the hole 92 as shown in FIG. 10, and then an implant 50 is implanted in the hole 92, and then an artificial tooth crown 60 is affixed to the implant 50, and thus the implant surgery is finished.

Figure 12:
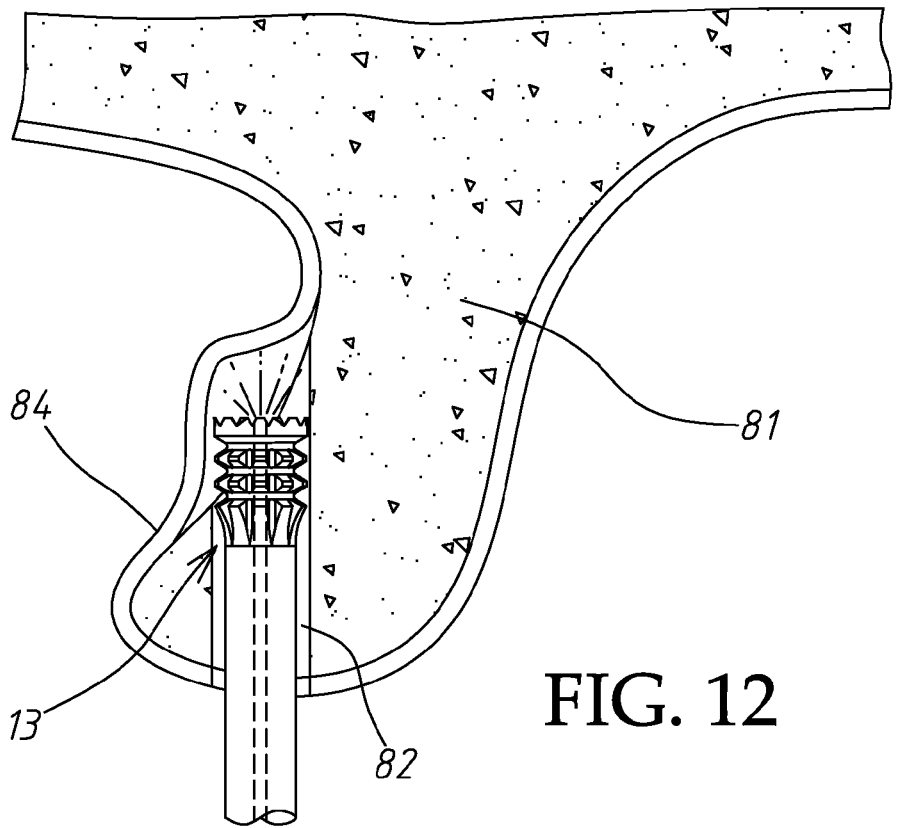
FIGS. 12 and 13 illustrate the ultrasonic sinus membrane/periosteum separation tool set of the present invention used in an upper jaw deformity implant surgery.
Figure 13:
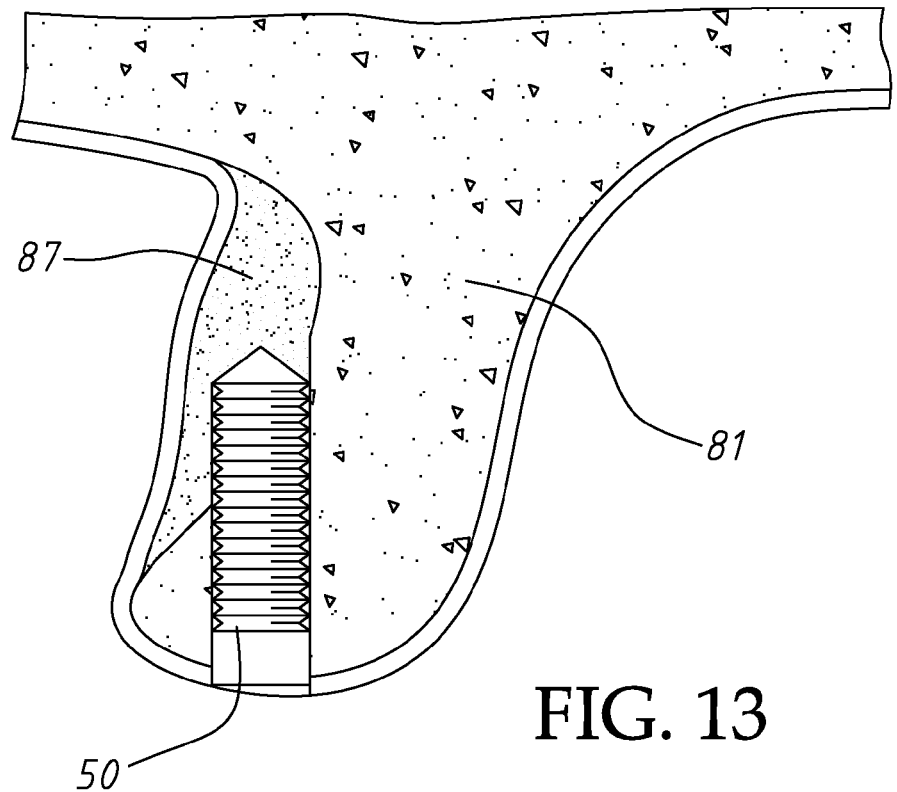

Further, the ultrasonic sinus membrane/periosteum separation tool set of the present invention can be used in upper or lower jaw deformity implant surgery. As shown in FIG. 12, the cutter tip 13 of the cutting tool 10 is inserted into a hole 82 on the alveolar ridge 81 of the deformed upper jaw to lift the periosteum 84, and then the spray nozzle 40 is used to enhance separation of the periosteum 83 (in the same manner as the aforesaid sinus membrane separation operation), and then the hole 82 is filled up with bone powder 87, and then an implant 50 is implanted in the alveolar ridge 81 of the deformed upper jaw.

Figure 14:
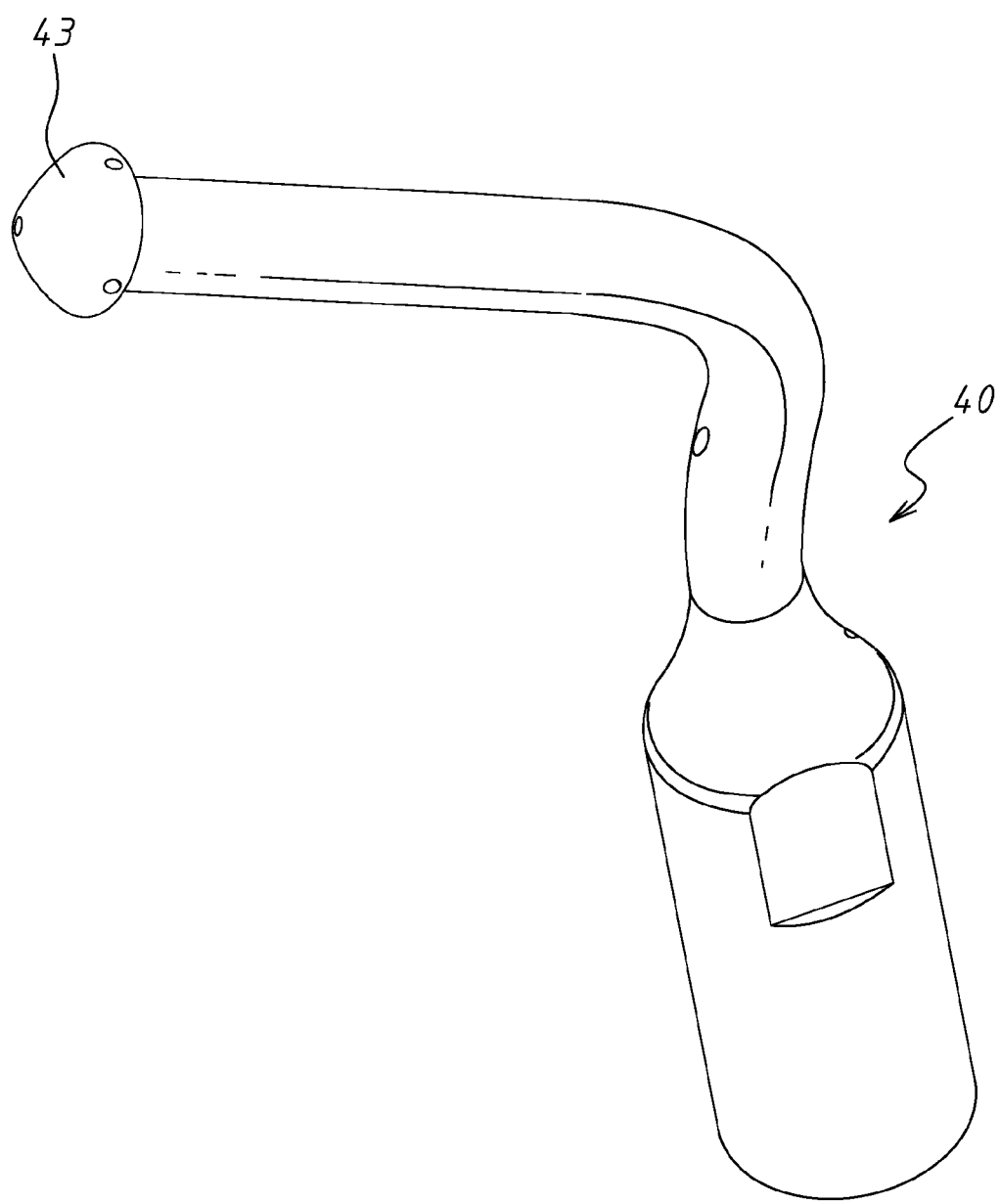
FIG. 14 is a schematic elevational view of an alternate form of the spray nozzle according to the present invention.
Figure 15:
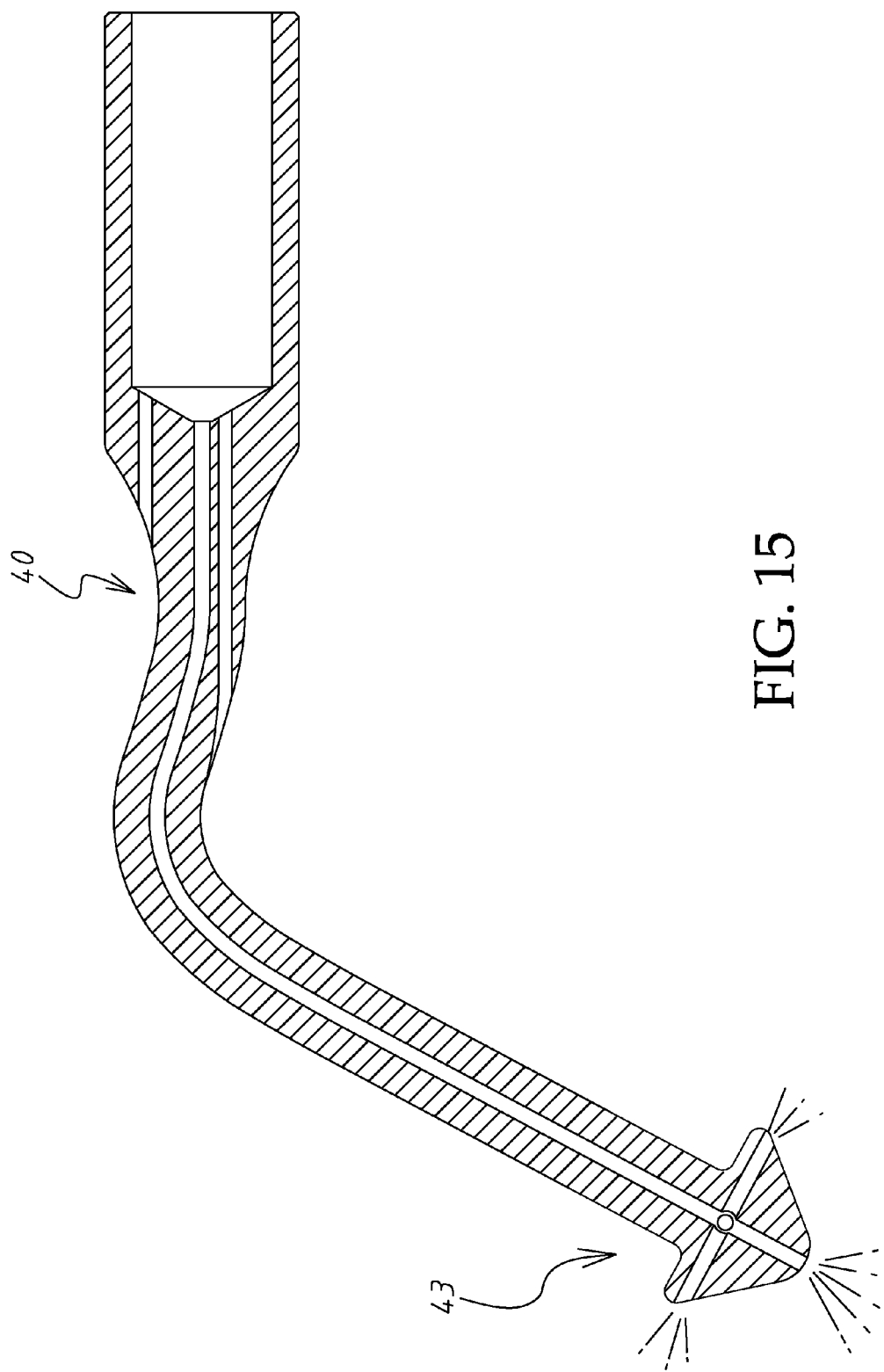
FIG. 15 is a sectional view of the spray nozzle shown in FIG. 14.

FIGS. 14 and 15 show an alternate form of the spray nozzle 40. This alternate form of spray nozzle is substantially similar to that shown in FIGS. 6 and 7 with the exception of that the operating tip 43 of this alternate form is shaped like a mushroom head.

Figure 16:
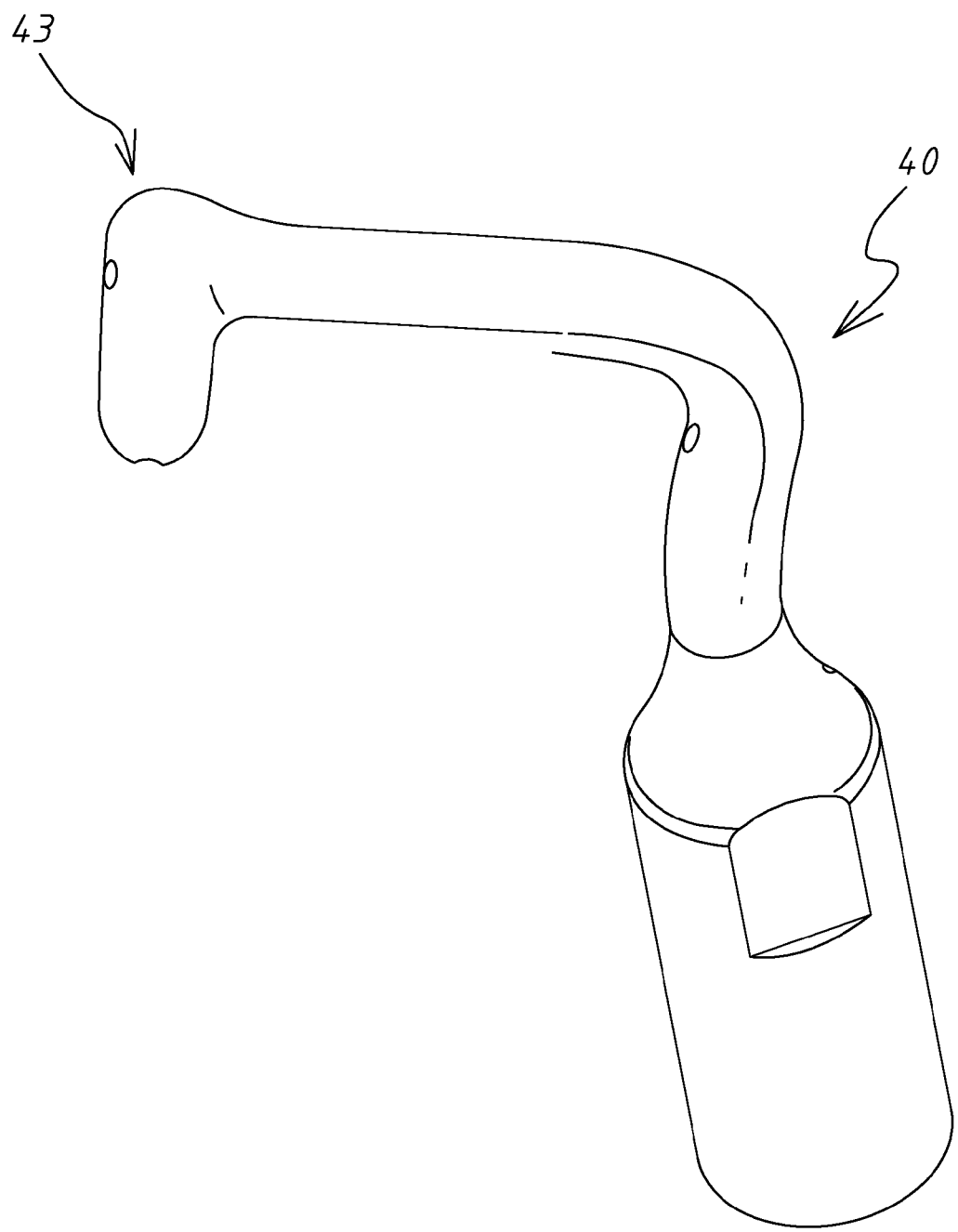
FIG. 16 is a schematic elevational view of another alternate form of the spray nozzle according to the present invention.
Figure 17:
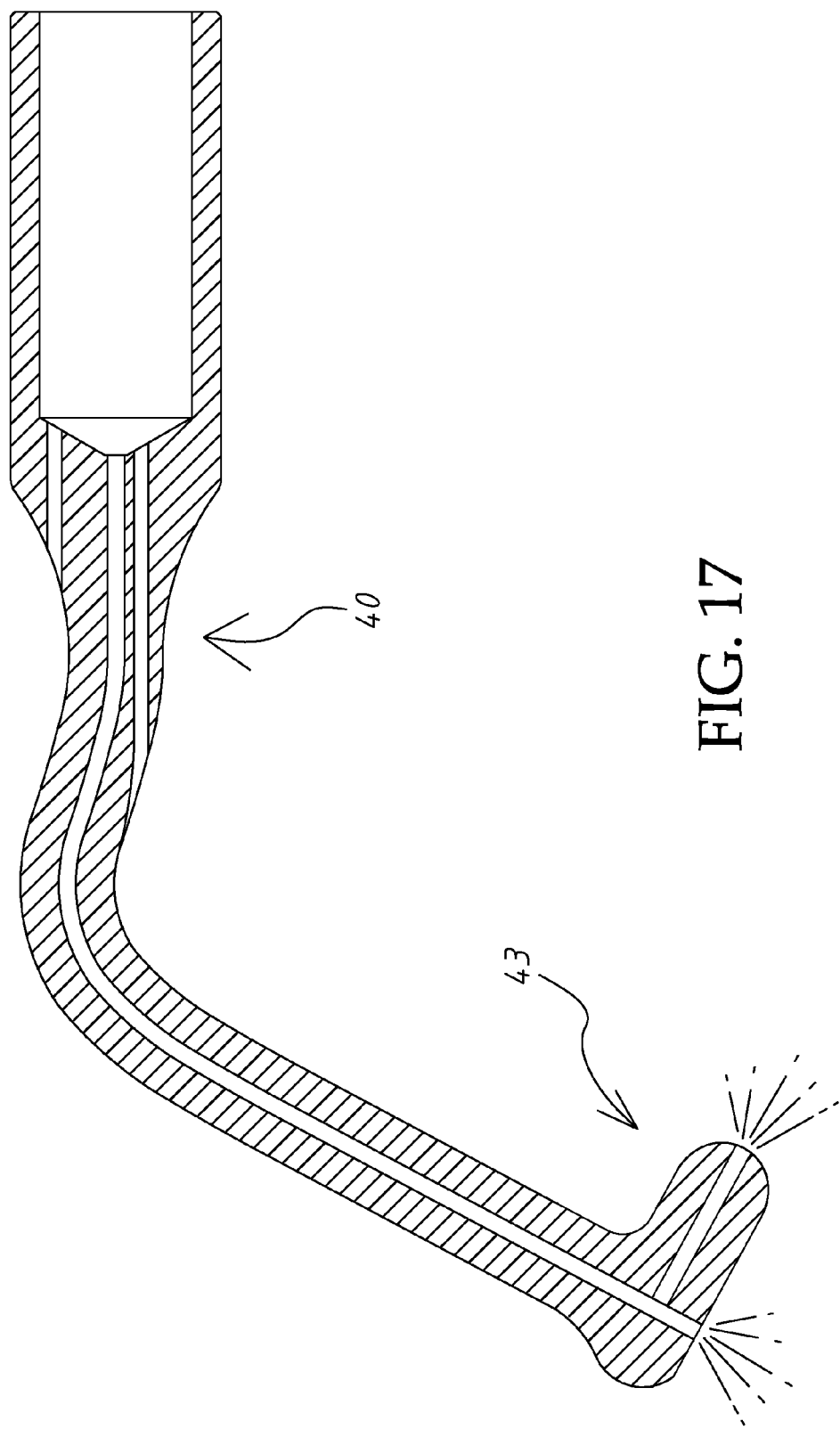
FIG. 17 is a sectional view of the spray nozzle shown in FIG. 16.

FIGS. 16 and 17 show another alternate form of the spray nozzle 40. This alternate form of spray nozzle is substantially similar to that shown in FIGS. 6 and 7 with the exception of that the operating tip 43 of this alternate is shaped like the Roman numeral 7.

Although particular embodiment of the invention have been described in detail for purposes of illustration, various modifications and enhancements may be made without departing from the spirit and scope of the invention. For example, the number of the jet holes 133 or 432 may be changed. Accordingly, the invention is not to be limited except as by the appended claims.

What the invention claimed is:

1. An ultrasonic sinus membrane/periosteum separation tool set for connection to a hand piece of an ultrasonic machine for use in a dental implant surgery, comprising: a cutting tool, said cutting tool comprising a connection base connectable to the hand piece of said ultrasonic machine, a pole extended from the connection base of said cutting tool, said pole having a longitudinal fluid passage extending through two distal ends thereof for passing of a fluid provided by said ultrasonic machine and a fluid injection hole for ejecting a fluid into a hole made on alveolar ridge of gingival of a patient, and a cutter tip located on one end of the pole of said cutting tool remote from the connection base of said cutting tool, said cutter tip having an end face, a plurality of protruding cutting edges raised from the end face of said cutter tip and periphery of said cutter tip, three jet holes located on the end face of said cutter tip and a plurality of oblique manifolds respectively connected between the jet holes of said cutter tip and the longitudinal fluid passage of the pole of said cutting tool; and a spray nozzle, said spray nozzle comprising a connection base, a pole extended from the connection base of said spray nozzle, said pole having a longitudinal fluid passage extending through two distal ends thereof for passing of a fluid provided by said ultrasonic machine and a fluid injection hole for ejecting a fluid into a hole made on the alveolar ridge of the gingiva of the patient to be treated, and an operation tip located on one end of the pole of said spray nozzle remote from the connection base of said spray nozzle for transferring ultrasonic waves from said ultrasonic machine to the fluid filled in a hole made on the alveolar ridge of the gingiva of the patient to be treated, said operation tip having a plurality of jet holes located on an end face and periphery thereof and respectively connected to the longitudinal fluid passage of the pole of said spray nozzle, wherein said cutting tool has a cooling fluid passage located on junction between the connection base and pole thereof for passing of a cooling fluid to cool down temperature of the junction; said spray nozzle has a cooling fluid passage located on junction between the connection base and pole thereof for passing of a cooling fluid to cool down temperature of the junction.

2. The ultrasonic sinus membrane/periosteum separation tool set as claimed in claim 1, wherein the poles of said cutting tool and said spray nozzle have a L-shaped configuration; the fluid injection hole of said cutting tool extends longitudinally through a part of the pole of said cutting tool adjacent to the turning angle of the L-shaped configuration of said cutting tool; the fluid injection hole of said spray nozzle extends longitudinally through a part of the pole of said spray nozzle adjacent to the turning angle of the L-shaped configuration of said spray nozzle.

3. The ultrasonic sinus membrane/periosteum separation tool set as claimed in claim 1, wherein the operating tip of said spray nozzle is shaped like a mushroom head.

4. The ultrasonic sinus membrane/periosteum separation tool set as claimed in claim 1, wherein the operating tip of said spray nozzle is shaped like the Roman numeral 7.

* * * * *